(12) United States Patent
Whiton et al.

(10) Patent No.: US 9,480,502 B2
(45) Date of Patent: Nov. 1, 2016

(54) EXPANSION INTERSPINOUS FIXATION DEVICE AND METHOD

(71) Applicant: SMOKEY MOUNTAIN SPINE, LLC, Coral Springs, FL (US)

(72) Inventors: Alan Whiton, Sevierville, TN (US); J. Scott Hay, Parkland, FL (US); Brian Haga, Bluff City, TN (US); Ryan Singh, Loxahatchee, FL (US)

(73) Assignee: Smokey Mountain Spine, LLC, Coral Springs, FL (US)

( * ) Notice: Subject to any disclaimer, the term of this patent is extended or adjusted under 35 U.S.C. 154(b) by 0 days.

(21) Appl. No.: 14/279,748

(22) Filed: May 16, 2014

(65) Prior Publication Data

US 2014/0343608 A1 Nov. 20, 2014

Related U.S. Application Data

(60) Provisional application No. 61/824,188, filed on May 16, 2013.

(51) Int. Cl.
*A61B 17/70* (2006.01)
*A61B 17/88* (2006.01)

(52) U.S. Cl.
CPC .................. *A61B 17/7068* (2013.01)

(58) Field of Classification Search
CPC .......... A61B 17/7062; A61B 17/7065; A61B 17/7067; A61B 17/7068
See application file for complete search history.

(56) References Cited

U.S. PATENT DOCUMENTS

| | | | | |
|---|---|---|---|---|
| 7,993,374 B2* | 8/2011 | Zucherman | ............ | A61K 31/37 606/249 |
| 8,048,118 B2* | 11/2011 | Lim | ................... | A61B 17/7062 606/248 |
| 8,142,479 B2* | 3/2012 | Hess | ................... | A61B 17/7065 606/248 |
| 8,241,330 B2 | 8/2012 | Lamborne et al. | | |
| 8,357,181 B2* | 1/2013 | Lange | ................ | A61B 17/7065 606/248 |
| 8,523,909 B2* | 9/2013 | Hess | ................... | A61B 17/7065 606/248 |
| 8,613,758 B2* | 12/2013 | Linares | ............. | A61B 17/7065 606/246 |
| 8,636,773 B2* | 1/2014 | Stern | ................... | A61B 17/7065 606/249 |
| 8,685,065 B1 | 4/2014 | Taber et al. | | |
| 8,702,757 B2* | 4/2014 | Thommen | .......... | A61B 17/7065 606/249 |

(Continued)

*Primary Examiner* — Jacqueline Johanas
(74) *Attorney, Agent, or Firm* — Laurence A. Greenberg; Werner H. Stemer; Ralph E. Locher

(57) ABSTRACT

A device and method for performing interspinous fixation or spinal fusion is provided. The device may generally include a first plate and a second plate, each having an adjustable length, and a mechanical actuator for increasing or reducing the length of the plates and, correspondingly, the device. Operation of the mechanical actuator causes first and second inner expansion portions of each plate to simultaneously slide on an outer fixed portion of the plate, to increase or decrease (depending on the direction of operation of the mechanical actuator) the separation between the first and second inner expansion portions, and thus, lengthen or shorten the plates and device.

10 Claims, 9 Drawing Sheets

(56) References Cited

U.S. PATENT DOCUMENTS

| | | | |
|---|---|---|---|
| 9,005,248 B2* | 4/2015 | Taber | A61B 17/7068 606/249 |
| 9,066,760 B2* | 6/2015 | Taber | A61B 17/7068 606/249 |
| 2007/0100340 A1* | 5/2007 | Lange | A61B 17/7065 606/279 |
| 2007/0233098 A1* | 10/2007 | Mastrorio | A61B 17/7065 606/86 A |
| 2007/0276500 A1* | 11/2007 | Zucherman | A61B 17/7053 623/17.16 |
| 2009/0125062 A1* | 5/2009 | Arnin | A61B 17/025 606/246 |
| 2009/0198282 A1* | 8/2009 | Fielding | A61B 17/7062 606/279 |
| 2009/0292316 A1* | 11/2009 | Hess | A61B 17/7065 606/249 |
| 2010/0004697 A1* | 1/2010 | Fortin | A61B 17/66 606/86 R |
| 2010/0036419 A1* | 2/2010 | Patel | A61B 17/7065 606/249 |
| 2010/0106190 A1* | 4/2010 | Linares | A61B 17/7065 606/249 |
| 2011/0144692 A1* | 6/2011 | Saladin | A61B 17/7053 606/249 |
| 2011/0190817 A1* | 8/2011 | Thommen | A61B 17/7065 606/249 |
| 2011/0313458 A1* | 12/2011 | Butler | A61B 17/7065 606/249 |
| 2012/0109204 A1* | 5/2012 | Linares | A61B 17/7065 606/249 |
| 2012/0253395 A1* | 10/2012 | Linares | A61B 17/7065 606/249 |
| 2012/0310292 A1* | 12/2012 | Smisson, III | A61B 17/7067 606/86 A |
| 2013/0012996 A1* | 1/2013 | Zamani | A61B 17/7068 606/248 |
| 2013/0079880 A1 | 3/2013 | Wolters et al. | |
| 2013/0158604 A1 | 6/2013 | Okamoto | |
| 2013/0184754 A1 | 7/2013 | Taber et al. | |
| 2013/0190820 A1* | 7/2013 | Siegfried | A61B 17/7068 606/248 |
| 2013/0296939 A1* | 11/2013 | Perkins | A61B 17/7068 606/249 |
| 2014/0371797 A1* | 12/2014 | Seifert | A61B 17/3468 606/279 |

* cited by examiner

EXPANSION INTERSPINOUS FIXATION DEVICE AND METHOD

CROSS-REFERENCE TO RELATED APPLICATIONS

The present application claims priority to: Provisional Patent Application No. 61/824,188, filed on May 16, 2013, entitled "EXPANSION INTERSPINOUS FIXATION DEVICE"; that application being incorporated herein, by reference, in its entirety.

BACKGROUND OF THE INVENTION

1. Field of the Invention

The present invention relates to a system, method and device for interspinous fixation or fusion and, more particularly, to an expandable interspinous fixation device, and a system and method for using such a device.

2. Description of the Related Art

Interspinous fixation, also called spinal fusion, is one of the more commonly performed surgeries for the treatment of chronic, severe lower back pain. For example, interspinous fixation is often used to treat conditions such as degenerative spondylolisthesis, in which one of the vertebrae slips forward or backward relative to the adjacent vertebra or vertebrae. Symptoms of degenerative spondylolisthesis can include severe lower back pain, decreased range of motion of the lower back, and numbness, tingling, or weakness in the legs due to nerve compression.

Currently used methods of treatment for this condition, and others affecting the spine, include vertebral fixation using intervertebral cages implanted with bone graft using supplemental posterior fixation via pedicle screws and rods to provide segmental stability until a biological fusion occurs. However, spine screws in such a method are positioned very close to nerve root and vasculature along the spine. Further, fluoroscopy is required to visualize screw placement within a patient's anatomy, thus exposing the patient to high levels of radiation.

In recent years, a number of interspinous process devices have been used that provide an interspinous fixation that can typically perform as well as the pedicle screw-rod systems, but with less risk of patient injury. Such devices are typically affixed to, for example, the processes of two adjacent vertebrae. However, these devices provide limited opportunity to incorporate an integral graft material to foster bone growth. Additionally, such interspinous process devices having fixed size limits are suitable for only some patients, but are unsuitable for the anatomy of many patients. These two limitations, in part, have played a role in discouraging broad acceptance from surgeons who could otherwise use these devices.

Accordingly, it is desirable to provide an interspinous fixation device that reduces the likelihood of patient injury, offers integrated graft material, and is well-suited to meet the anatomical needs of practically any patient.

SUMMARY OF THE INVENTION

The present invention advantageously provides a device, system and method for interspinous fixation. The device may generally include a first plate and a second plate, each of the first and second plates having an adjustable length, and a mechanical actuator for increasing or reducing the length of the device. In one particular embodiment, each of the first and second plates is made up of a plurality of sub-plates or portions. In one particular embodiment, this plurality of sub-portions includes an outer fixed portion, and first and second inner expansion portions that slide (along or parallel to the longitudinal axis through each plate) on the outer fixed portion in order to be moved relative to one another. Operation of the mechanical actuator causes the first and second inner expansion portions to simultaneously slide on the outer fixed portion to increase or decrease (depending on the direction of operation of the mechanical actuator) the separation between the first and second inner expansion portions.

The method may generally include enclosing the spinous process of each of two adjacent vertebra between a first plate and a second plate of an interspinous fixation device, at least a portion of an inner surface of each of the first plate and second plate having a plurality of studs, and adjusting the length of each of the first and second plates such that at least a portion of each of the two adjacent vertebrae are clamped between the plurality of studs of each of the first and second plates.

Other features, which are considered as characteristic for the invention, are set forth in the drawings and the appended claims.

Although the invention is illustrated and described herein as embodied in an expansion interspinous fixation device and method, it is nevertheless not intended to be limited to the details shown, since various modifications and structural changes may be made therein without departing from the spirit of the invention and within the scope and range of equivalents of the claims.

The construction of the invention, together with additional objects and advantages thereof, will be best understood from the following description of the specific embodiment when read in connection with the accompanying drawings.

BRIEF DESCRIPTION OF THE SEVERAL VIEWS OF THE DRAWINGS

For a fuller understanding of the nature of the present invention reference should be made to the following detailed description taken in connection with the accompanying drawings in which like reference numbers represent like elements, wherein.

DETAILED DESCRIPTION OF THE PREFERRED EMBODIMENT

An interspinous fixation device (which may also be referred to as an "interspinous anchor," a "spinous fixation system," or a "spinal interlaminal fixation orthosis") is provided which may be used on adjacent spinous processes (as shown, for example, in FIGS. 1 and 2) to perform interspinous fixation or fusion as a minimally invasive alternative to pedicle screw instrumentation in a variety of treatment procedures. In humans, the spinous process of each vertebra is a portion of the vertebra that is directed backward and downward from the junction of the laminae and serves as a point of attachment for muscles and ligaments.

Figure 1:
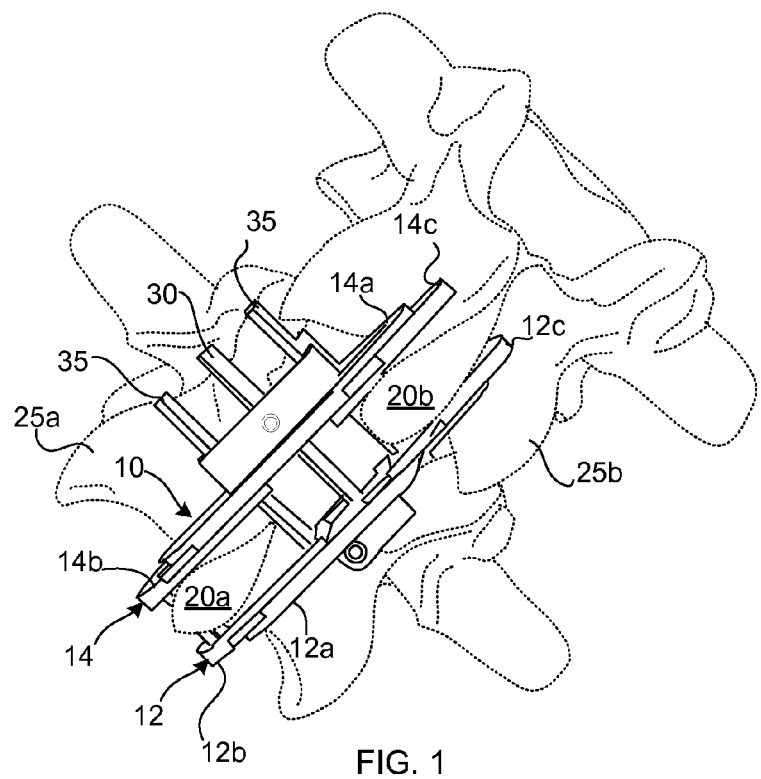
FIG. 1 is a perspective view, taken from the top, of an interspinous fixation device according to one particular embodiment of the present invention, wherein the device is affixed to the spinous processes of two adjacent vertebrae.
Figure 2:
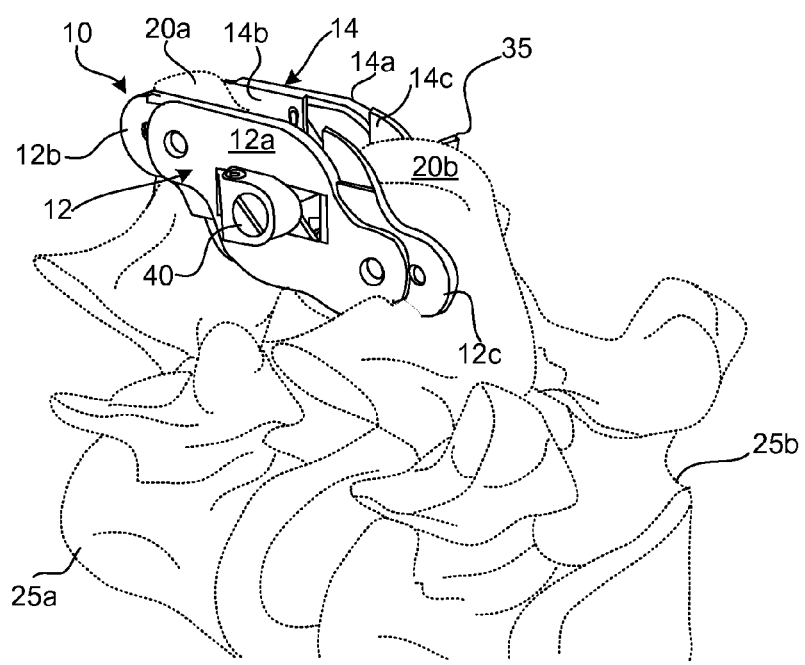
FIG. 2 is a perspective view, taken from the side, of the interspinous fixation device of FIG. 1, the device being affixed to the processes of two adjacent vertebrae.

Referring now to FIGS. 1 and 2, an interspinous fixation device 10 according to one particular embodiment of the present invention is shown affixed to the spinous processes 20a, 20b of two adjacent vertebrae 25a, 25b. The device 10 generally includes a first plate 12 and a second plate 14 joined by a plurality of rods. In the present particular embodiment illustrated in FIGS. 1 and 2, the first and second plates 12, 14 are joined by a flattened expansion rod 30 and a plurality of guide rods 35. However, this is not meant to be limiting as more or fewer rods and/or different types of rods may be used without departing from the spirit of the present invention. For example, as will be seen below in connection with the embodiment of FIGS. 5-6, two expansion/guide rods 135 are used instead of the flattened expansion rod 30 and the plurality of guide rods 35 of FIGS. 1 and 2. Other expansion mechanisms can additionally be used, as desired.

Referring back to FIGS. 1 and 2, each of the first plate 12 and second plate 14 is made up of a plurality of sub-plates or portions that permit expansion to be performed in response to movement of a mechanical actuator. For example, the first plate 12 is made up of two inner expansion portions or portions 12b and 12c mechanically connected to an outer fixed portion or portion 12a, and, in fact, are mounted so as to slide on the fixed outer plate 12a. Similarly, the second plate 14 is made up of two inner expansion portions or portions 14b and 14c mechanically connected to (i.e., slidably mounted on) an outer fixed portion or portion 14a. The inner expansion portions 12b, 14b are movable relative to the inner expansion portions 12c, 14c, upon movement of the actuator. Thus, the inner expansion portions 12b, 14b and 12c, 14c can be moved relative to the outer fixed plates 12a, 14a, and to one another, in order to expand (lengthen) or, if already expanded to some degree, to retract (shorten) the respective plates 12, 14. As will be discussed in more detail in connection with specific exemplary embodiments herebelow, according to the present invention, a mechanical actuator is used to control the movement of the inner expansion portions 12b, 12c and 14b, 14c, and to maintain their relative positions to one another. According to the terminology used herein, the device is expanded or lengthened when the separation between the inner expansion portions is increased, and the device is retracted or shortened when the separation between the inner expansion portions is reduced. The device is described as being in the fully retracted configuration when the inner expansion portions have no separation therebetween (i.e., they abut one another).

Although the present preferred embodiments are described as including two sliding/moving inner expansion portions 12b, 12c and 14b, 14c per plate 12, 14, it should be understood that, if desired, any of the embodiments described herein could also be modified such that, for each of the first and second plates, only one inner expansion portion moves relative to the other inner expansion portion (the position of which would be fixed) without departing from the spirit and scope of the present invention. However, in terms of the present invention, it is more preferred that both inner expansion portions be movable relative to one another.

In use, after insertion and placement relative to the spinous processes 20a, 20b of two adjacent vertebrae 25a, 25b of interest, the first plate 12 and the second plate 14 are adjusted (expanded or retracted) to fit the anatomy of the patient using an actuator. In the presently illustrated embodiment, this is done by rotating an actuator screw 40 that is in communication with the expansion rod 30, which rotates to separate or retract the inner expansion portions 12a, 12b and 14a, 14b relative to one another. After the device 10 is fitted to the anatomy of the patient, the first plate 12 and second plate 14 are tightened and locked in position against either side of the spinous processes 20a, 20b. If desired, after the plates are tightened and locked on the spinous processes 20a, 20b, the actuator can be used (rotation of the actuator screw 40, in the present example) to further separate the plates 12, 14 so as to increase the distance between (i.e. distract) the adjacent vertebrae. As a consequence of the actuator, the device 10 is self-locking, no further locking mechanism is needed to maintain the expanded plates 12, 14, at their expanded lengths.

Once the device 10 is implanted, graft material may be added to the space between the first plate 12 and second plate 14, so as to be positioned in contact with one or more vertebrae. The combination of the device placement and the graft material disposed within the device 10 eventually will lead to the fusion of the vertebrae 25a, 25b connected by the device. Particular embodiments of an interspinous fixation device that can be used as described in connection with device 10 are shown and explained in greater detail in connection with FIGS. 3-4 and 5-6.

Figure 3:
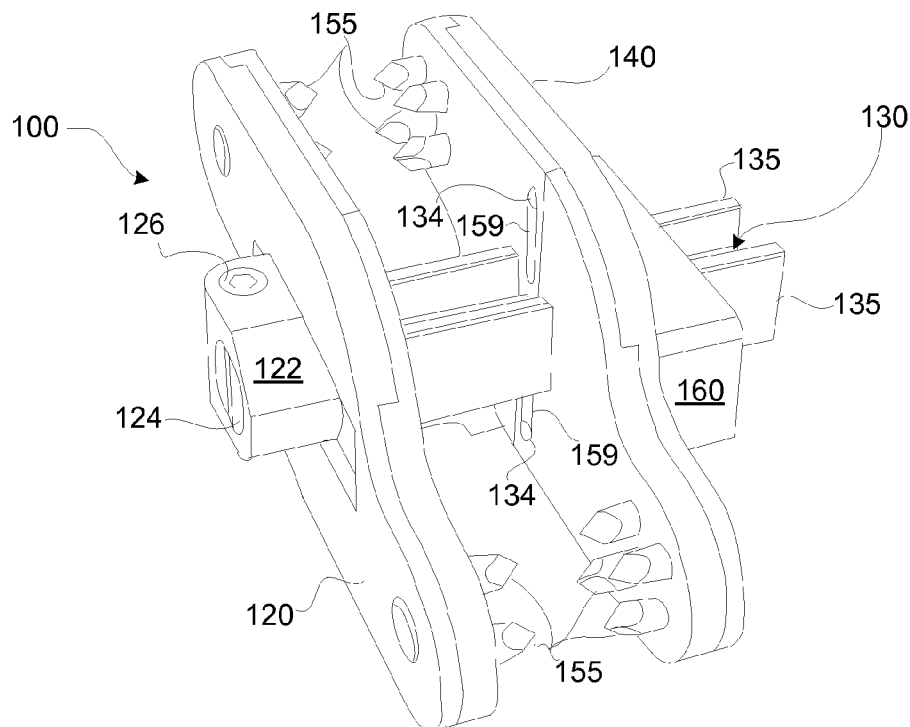
FIG. 3 is a perspective view of an interspinous fixation device according to another particular embodiment of the present invention, wherein the device is illustrated in a retracted configuration.
Figure 4A:
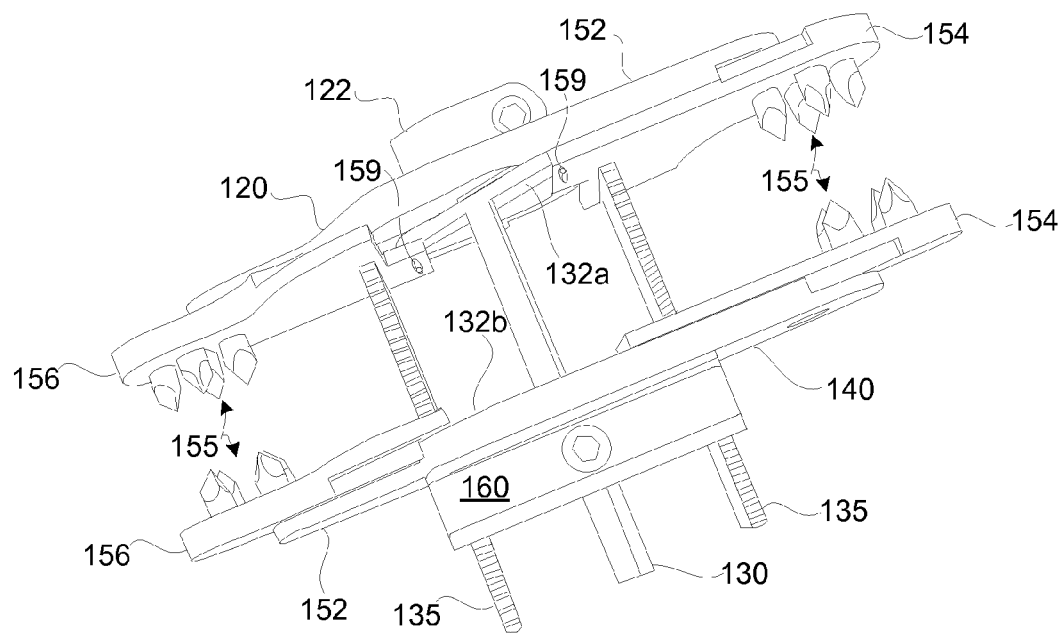
FIG. 4A is an overhead perspective view of an interspinous fixation device according to one particular embodiment of the present invention, wherein the device is illustrated in an expanded configuration.
Figure 4B:
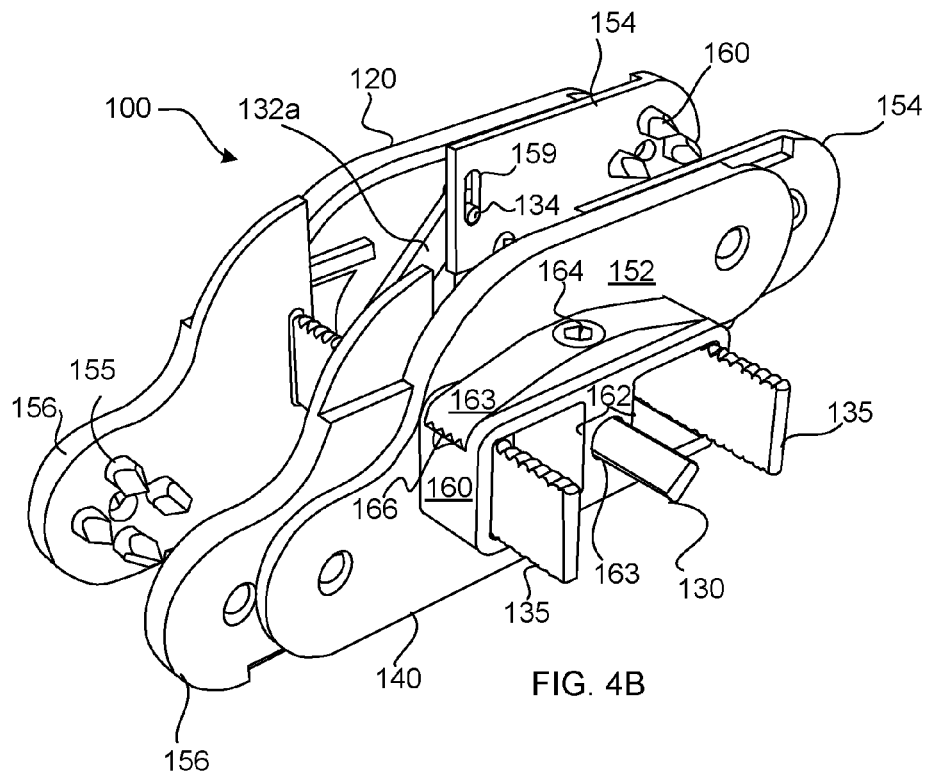
FIG. 4B is an isometric view of the device shown in FIG. 4A.

Referring now to FIGS. 3-4B, a particular embodiment of an interspinous fixation device 100 is shown and described in greater detail. FIG. 3 shows the device in a fully retracted configuration and FIGS. 4A-4B show the device in an expanded configuration, which can be any configuration having an inner expansion portion separation up to, and including, a fully expanded configuration of the device 100, depending on the anatomy of the patient. For example, the device 100 may be partially expanded for fixation of vertebrae (25a, 25b of FIGS. 1 and 2) with an average space between adjacent spinous processes, and in a fully retracted configuration for fixation of vertebrae with a smaller-than-average space between adjacent spinous processes. The device 100 may be composed of biocompatible materials such as titanium, stainless steel, and/or polyetheretherketone (PEEK), although other materials may also be used.

As shown in FIGS. 3-4B, the device 100 of the present embodiment generally includes a first plate 120 and a second plate 140 separated by a plurality of guide rods 135. Expansion of the plates 120 and 140 are controlled by an actuator, which, in the present embodiment, includes two arms 132a, 132b arranged in a double "T" configuration around the expansion rod 130 (i.e., with the bars of the two "T"s aligned with one another and perpendicular to the longitudinal axis of the expansion rod). In one particular embodiment of the invention, the actuator arm 132a is fixed at one end of the expansion rod 130 and the second actuator arm 132b is slidable on the expansion rod 130. In this particular embodiment, the expansion rod 130 is flattened and passes through a hole in the second actuator arm 132b having the same cross-sectional shape as the expansion rod 130, so that the second actuator arm 132b can slide on, but not rotate around, the expansion rod 130. Thus, rotation of the flattened expansion rod 130 turns both actuator arms 132a and 132b simultaneously, and in a defined manner.

Each of the first plate 120 and second plate 140 are configured to include an outer fixed portion or portion 152 which has first and second inner expansion portions or portions 154, 156, respectively, slidably attached thereto. One pin 134 at each end of each actuator arm 132a, 132b is linked into a slot 159 in a respective one of the inner expansion portions 154, 156, and acts as a cam to move the inner expansion portions 154, 156 relative to one another upon rotation of the actuator arms 132a, 132b. Thus, rotation of the actuator arms 132a, 132b drives the pins 134 in the linear (elongated) slots 159 causing a linear sliding movement of the inner expansion portions 154, 156. Additionally, each of the first and second inner expansion portions 154, 156 includes a plurality of fixing studs 155 at a distal end portion. Each of the fixing studs 155 may have a sharp, pointed end that may engage (that is, penetrate) bones, such as a spinous process (such as 20a, 20b of FIGS. 1 and 2).

The actuator mechanism of the device 100 includes a housing 122 located adjacent to, or on, the outer fixed portion 152 of the first plate 120. The housing 122 is sized to accept an actuator screw 124 that is in communication with the expansion rod 130. Rotation of the actuator screw 124 causes rotation of the actuator arms 132a, 132b to expand or retract the inner expansion portions 154, 156 of the first and second plates 120, 140, as shown and described in greater detail in connection with FIGS. 4A and 4B. If desired, the actuator screw 124 can be engaged to a worm gear 126, also in the housing 122, that is rotatable through the use of a tool to rotate the actuator screw 124. Alternately, the actuator screw 124 can be driven directly using a tool sized to engage a head of the actuator screw 124, accessible through the housing 122. The engagement of the worm gear 126 and the actuator screw 124 helps to maintain the arms 132a, 132b, in their current positions, thus maintaining a current expanded or retracted configuration of the device 100.

Continuing to refer to FIGS. 3-4B, the outer fixed portion 152 of the second plate 140 may include a frame 160 having two apertures 162 through which the guide rods 135 are disposed, and a third aperture 163 through which the expansion rod 130 is disposed, as shown. As with the expansion rod 130, described above, each of the guide rods 135 may be flattened, having a height that is greater than a width; however, the height of the guide rods 135 may be greater than the height of the expansion rod 130, as shown. Other configurations of rods may also be used, if desired. Additionally, in the present particular embodiment, the length of each of the guide rods 135 is at least great enough to extend from the first plate 120 to the outer portion of the second plate 140 or beyond the outer portion of the second plate 140. Each of the guide rods 135 and expansion rod 130 may include a first end and a second end, with the first end being coupled to the first plate 120.

As shown for example in FIG. 4A, the first end of a first guide rod 135 may be affixed to the first inner expansion portion 154 of the first plate 120, and the first end of a second guide rod 135 may be affixed to the second inner expansion portion 156 of the first plate 120. Additionally, the first end of the expansion rod 130 may be affixed to the actuator screw 124 proximal to an inner surface of the outer fixed portion 152 of the first plate 120. Further, the first and second inner expansion portions 154, 156 of the first plate 120 may be configured to abut or substantially surround the expansion rod 130 when the device 100 is in the fully retracted configuration, as shown in FIG. 3.

If desired, each guide rod 135 may also have at least one ridged or serrated edge (for example, along the guide rod width, as shown in FIGS. 4A-4B). Although the guide rods are shown in FIG. 3 as having smooth edges, the guide rods of the device shown in FIG. 3 may also have at least one ridged or serrated edge, as shown in FIGS. 4A-4B. In one particular embodiment of the invention, the frame affixed 160 to the outer portion 152 of the second plate 140 includes a lateral spring loaded ratchet locking mechanism 163, which may be seated within the frame 160 and which engages the at least one serrated edge of each guide rod 135 to lock the width of the device 100. As shown in FIG. 4B, the ratchet locking mechanism 163 may be set into the frame 160 and tightened against the guide rods 135, such that ridges or serrations 166 of the ratchet locking mechanism 163 engage the serrations on the guide rods 135. Once the proper device length is established, the ratchet locking mechanism 163 may be tightened against the guide rods 135 by rotating a locking screw 164. As a non-limiting example, the locking screw 164 may include a hexagonal socket in its head, although other mechanisms may be used.

When in an expanded configuration, the first plate 120 and second plate 140 of the device 100 may be manually separated from one another a distance sufficient for the spinous processes of interest to be received therebetween. The device 100 may be positioned such that the fixing studs 155 engage at least a portion of each of the adjacent spinous processes (See FIGS. 1 and 2). If the device 100 needs to be adjusted from the retracted configuration to the expanded configuration, or vice versa, or to a configuration therebetween, the actuator screw 124 may be rotated using a tool configured to engage the head of the actuator screw 124. As discussed above, rotation of the actuator screw 124 will likewise rotate the flattened expansion rod 130. Thus, as the actuator screw 124 is rotated, the configuration of the actuator rod 130 and the arms 132a, 132b, cause the arms 132a, 132b to rotate about the same longitudinal axis as the actuator rod 130. This rotation causes the pins 134 to slide in the elongate slot or aperture 159 as the arms rotate, thus acting as a cam mechanism to separate or pull together the inner plates 154, 156. In the fully retracted configuration shown in FIG. 3, the longitudinal axis of the arms 132a, 132b may be substantially orthogonal to an axis along the widest part first and second plates. In an expanded configuration, the longitudinal axis of the arms 132a, 132b may be rotated by between approximately 10° and approximately 90° (for example, as shown in FIG. 4A). As the arms 132a, 132b rotate in a counterclockwise direction, the two inner expansion portions 154, 156 of each of the plates 120, 140, are pushed away from each other. Because the first end of each guide rod 135 is affixed to one of the two inner expansion portions 154, 156 of the first plate 120, lateral movement of the inner expansion portions 154, 156 of the second plate will also help move the inner expansion portions 154, 156 of the first plate 120 to move away from each other, and the device 100 is widened. Conversely, rotation of the arms 132a, 132b in a clockwise direction pulls the inner expansion portions of the first and second plates toward each other, thereby reducing the length of the device 100. As a non-limiting example, the length of the device 100 may be approximately 6 mm in the retracted configuration and approximately 18 mm in the expanded configuration.

Referring to FIG. 4B, the device 100 may include a ratcheting and/or locking mechanism disposed on or adjacent to the outer surface of the second plate 140. In one particular embodiment of the invention, the ratcheting/locking mechanism includes a frame 160 on the outer surface 152 of the second plate 140 configured to accept the expansion rod 130 and first and second guide rods 135 therethrough, and to accommodate movement of the rods 130, 135 when the device 100 is transitioned between the retracted configuration and an expanded configuration. As described above, rotation of the actuator screw may also rotate the flattened expansion rod 130. The actuator rod aperture 163 of the frame 160 may therefore be circular to allow free range of rotation. The two guide rod apertures 162 may be substantially rectangular or substantially square shaped, each having a width that is several times greater than the width of each guide rod 135, to allow lateral movement of the flattened guide rods 135 as the device 100 is transitioned between the retracted configuration and the expanded configuration. Further, each guide rod aperture 162 may have a height that is only slightly greater than the height of each guide rod 135 to prevent movement in non-lateral directions.

In an exemplary method, the spinous processes of two or more vertebrae of interest may be accessed using any currently known method (for example, ALIF or TLIF methods). However, a procedure that is less invasive than many currently known methods may be used in conjunction with this device, since only a small incision is required to position the device, and use of the device may provide equal or greater biomechanical stability to the treated spinal segment than use of more invasive procedures with additional instrumentation. Once the spinous processes of interest are accessed, the first plate and second plate of the interspinous fixation device described herein may be manually separated to a distance that will accommodate the width of the spinous processes. This width is particular to the anatomy of the patient.

Figure 9:
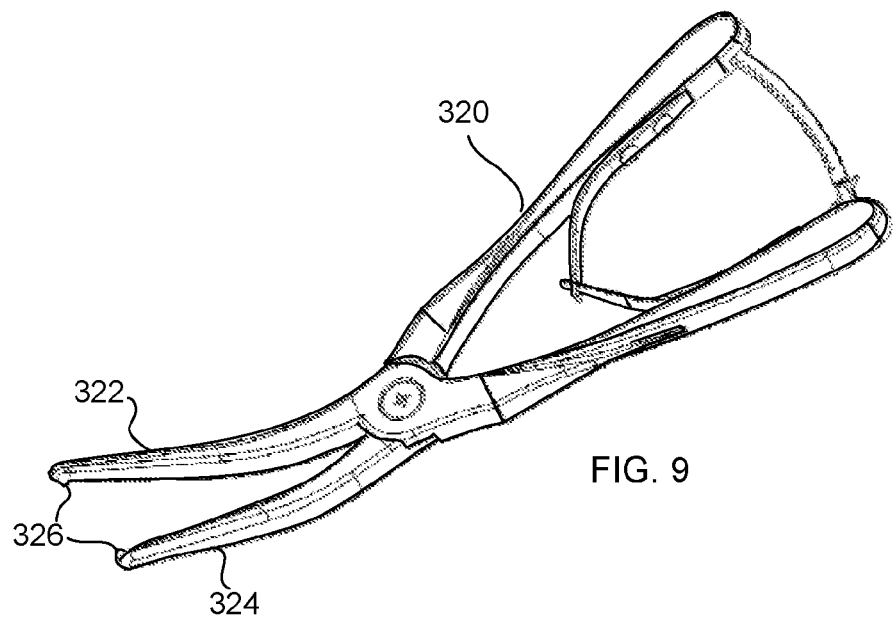
FIG. 9 is a perspective view of a clamp for use with an interspinous device according to one particular embodiment of the present invention.
Figure 10:
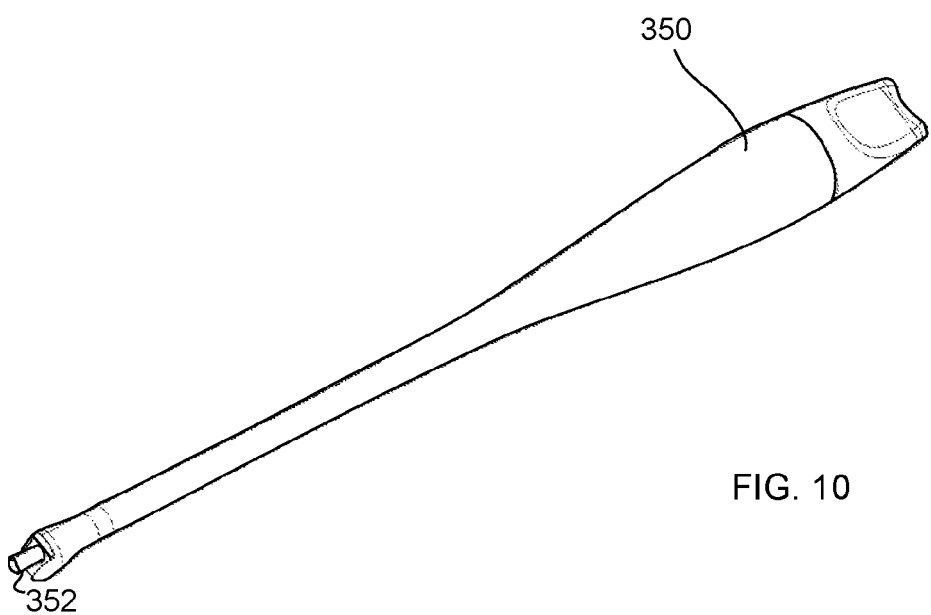
FIG. 10 is a perspective view of a tool for use with an interspinous device according to one particular embodiment of the present invention.

Once the plates 120, 140 are separated to a sufficient distance, the device 100 is positioned on the spinous processes such that the fixing studs 155 of the inner expansion portions 154, 156 of the first and second plate 120, 140 may be in contact with at least a portion of each spinous process. For example, the device 100 may be positioned using an implant delivery instrument that attaches to the interspinous fixation device. Further, the guide rods 135 and actuator rod 130 may be disposed between the adjacent processes, so that they do not interfere with the patient's anatomy (as shown in FIGS. 1 and 2). If adjustment of the length of the plates 120, 140 of the device 100 is required to place the fixing studs 155 in contact with the adjacent processes, the device may be expanded or retracted as appropriate by rotation of the actuator screw 124. Again, the appropriate device length will be determined by individual patient anatomy. Once the fixing studs 155 of the device 100 sufficiently line up with each of the adjacent processes, one or more compression clamps may be used to provide a compression force on the first plate 120 and second plate 140 of the device, thereby squeezing the interspinous fixation device 100 tightly about the adjacent processes such that the fixing studs 155 penetrate the bone. A ratchet locking mechanism 163 including grooves or teeth arranged complementary to serrations in the guide rails 135 allows the second plate 140 to be ratcheted towards the first plate 120 during squeezing with a clamping device. Note that the device 100 includes holes that can be used with a particularly designed clamping tool, shown in FIG. 9, if desired.

Once a desired width between the first and second plates 120, 140 has been achieved, the ratcheting mechanism can be further locked using a locking screw 164. More particularly, the locking screw 164 may be rotated to tighten the ratchet locking mechanism 163 down on the serrated guide rods 135, thereby locking the interspinous fixation device 100 in place. Once the device 100 is in place, spinal distraction may be accomplished by rotating the actuator screw 130 to increase the distance between (i.e. distract) the adjacent vertebrae. Graft material (allograft or autograft) may be inserted into the space created between the first plate 120 and second plate 140 of the device 100 when the first and second plates 120, 140 are spread a distance apart by the spinous processes of adjacent vertebrae. Graft material may also be inserted in spaces around the device 100. The combination of the device placement and the graft material disposed within the device eventually will lead to the fusion of the vertebrae connected by the device 100.

Figure 5:
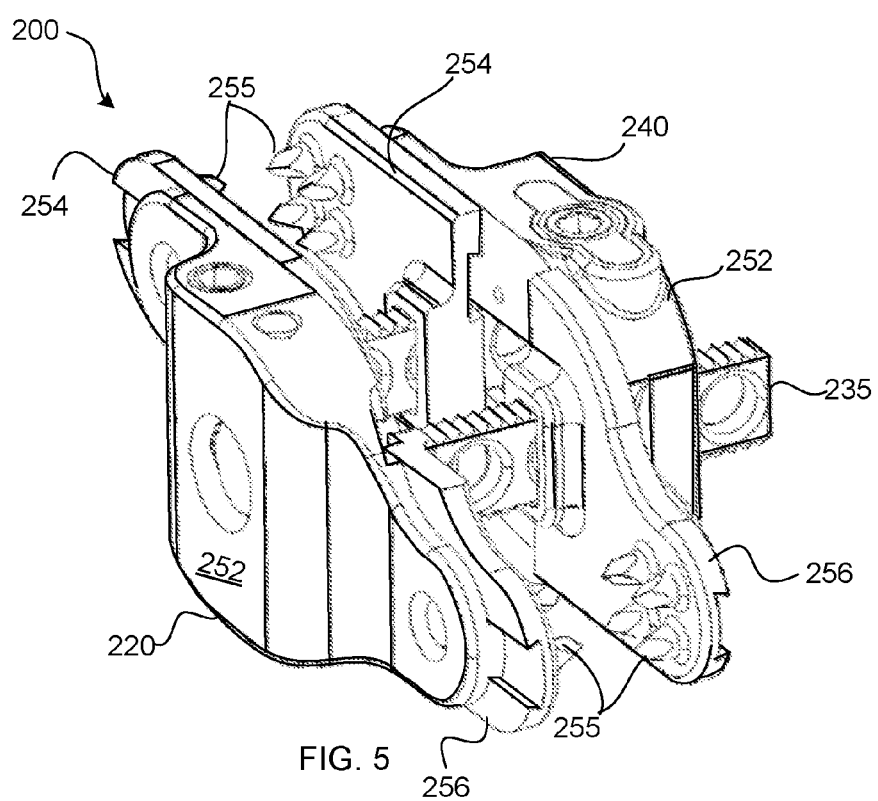
FIG. 5 is an isometric view of an interspinous fixation device according to a further particular embodiment of the present invention, the device being illustrated in an expanded configuration.
Figure 6A:
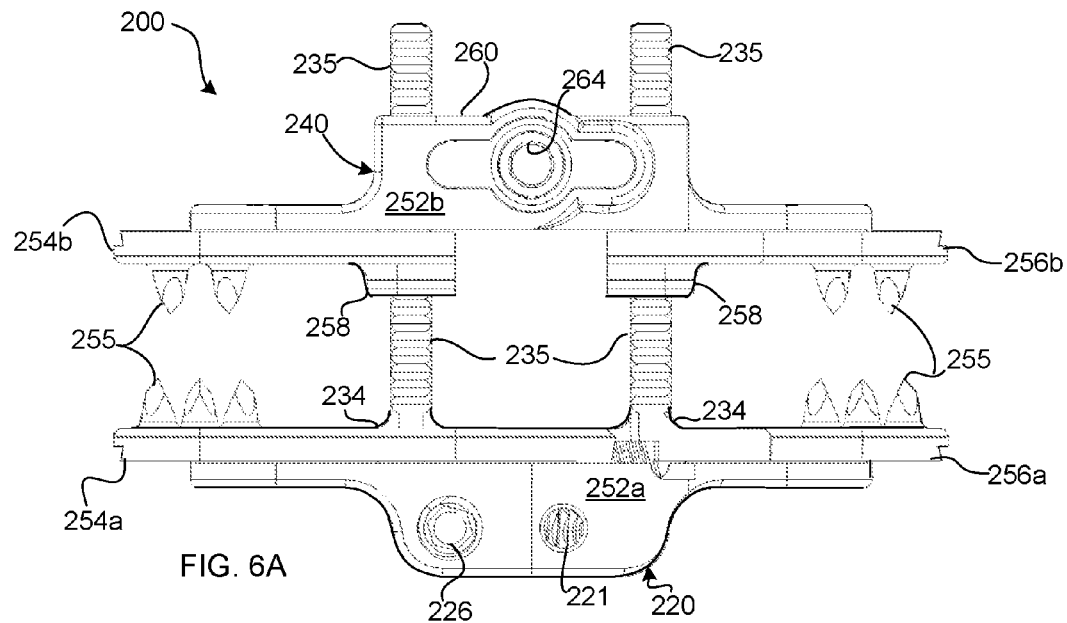
FIGS. 6A and 6B are top and bottom plan views, respectively, of the device of FIG. 5, shown in an expanded configuration.
Figure 6B:
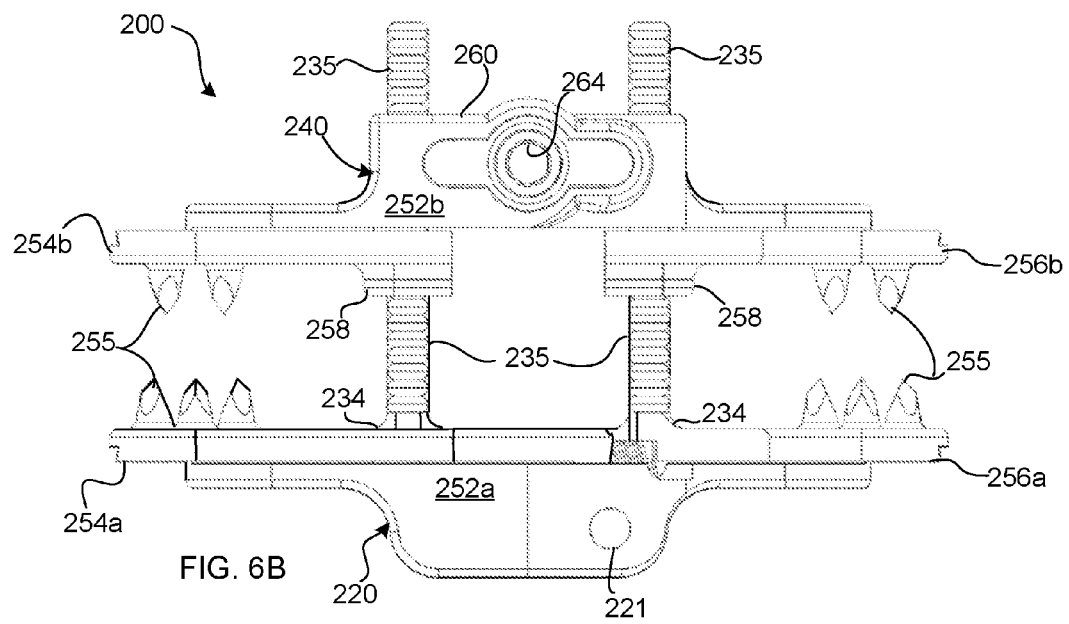
Figure 6C:
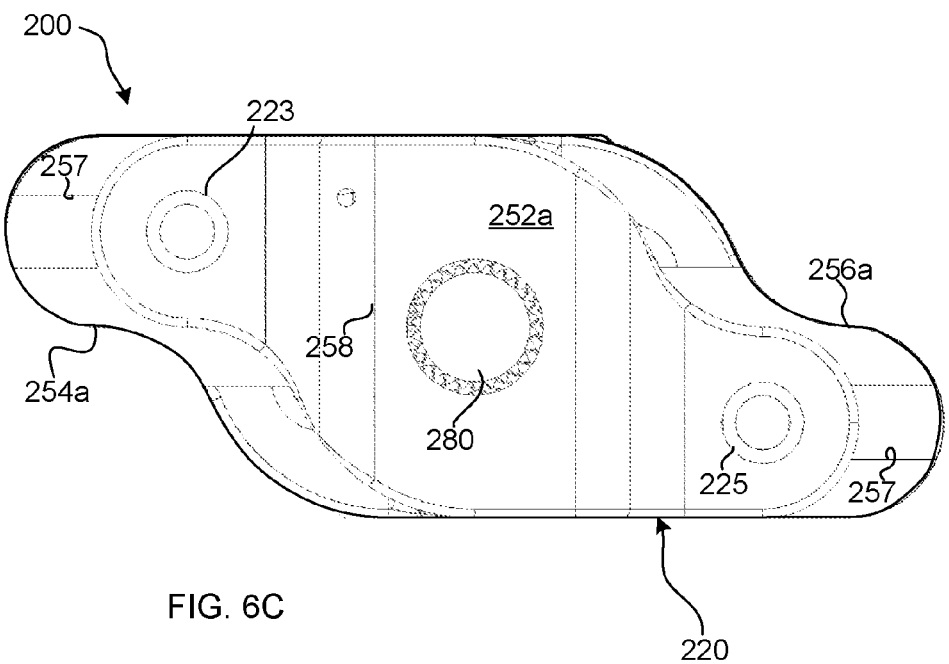
FIGS. 6C and 6D are front and back plan views, respectively, of the device of FIG. 5, shown in an expanded configuration.
Figure 6D:
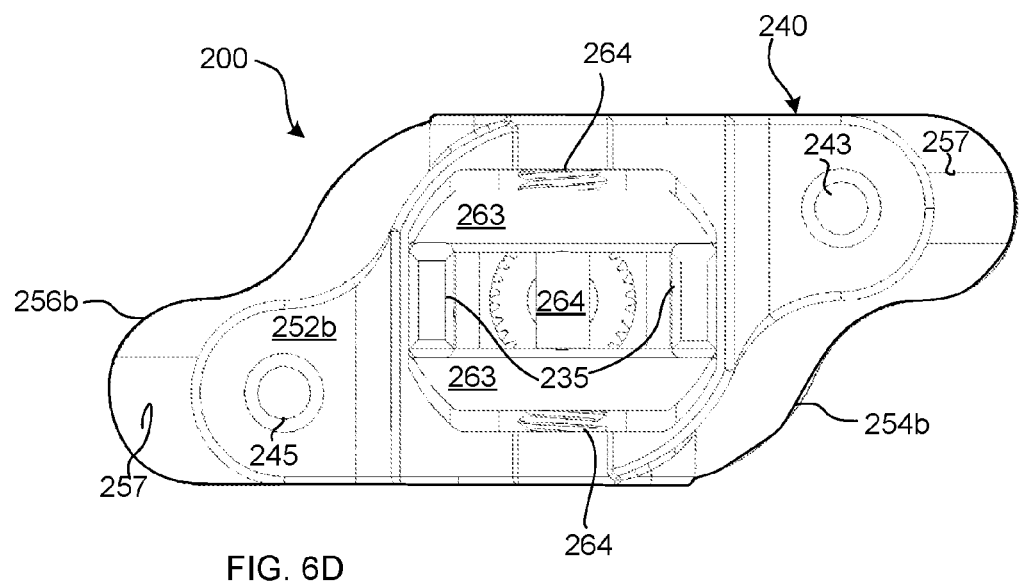
Figure 6E:
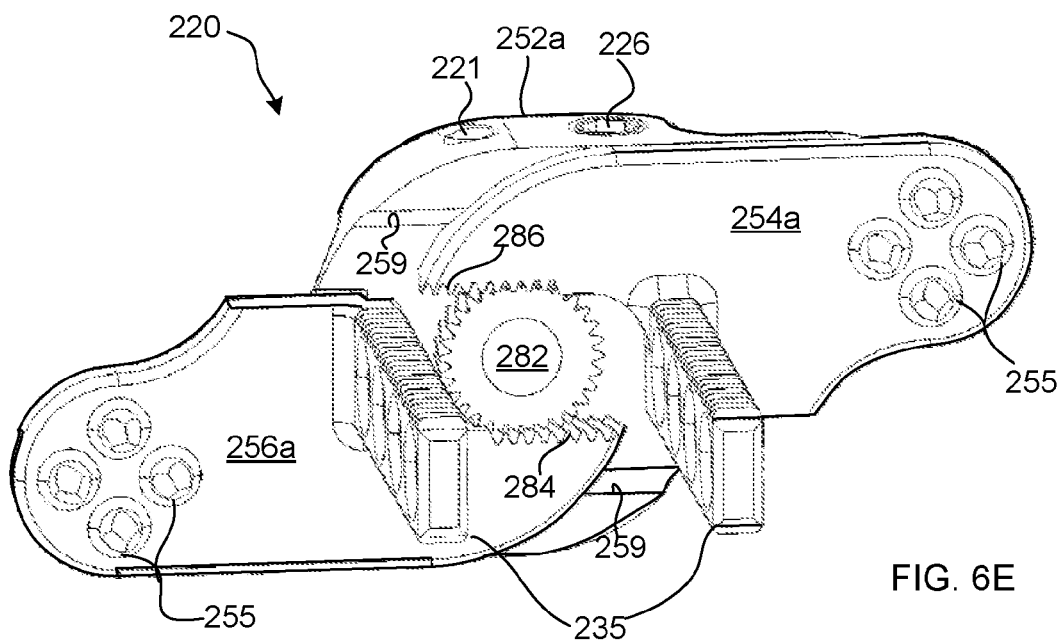
FIG. 6E is a partial view of the device of FIG. 5, having a portion of the back plate and the clamp mechanism removed.
Figure 6F:
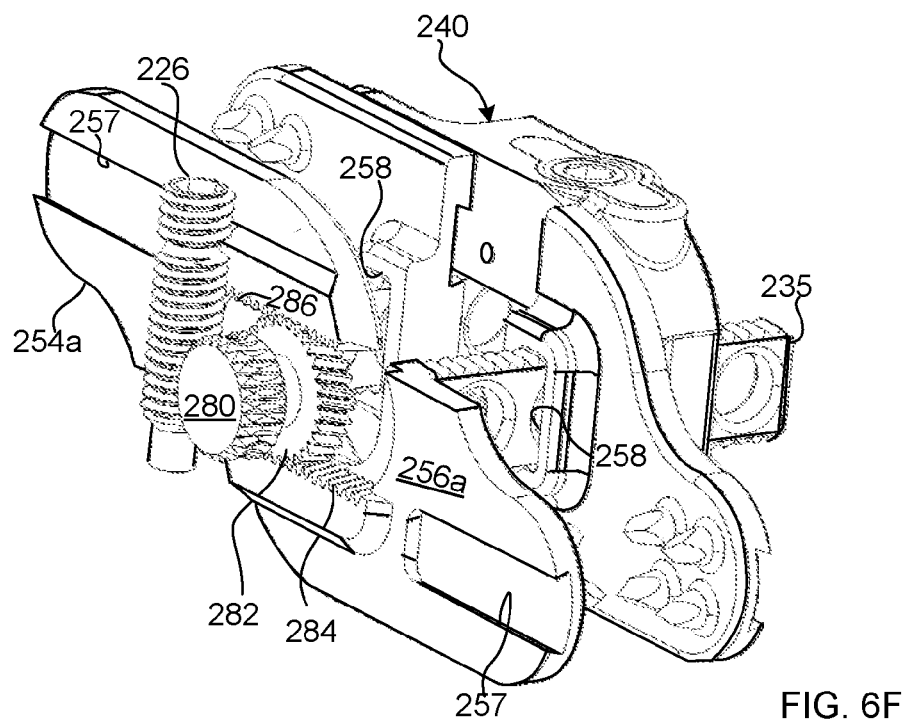
FIG. 6F is a partial view, having a portion of the front plate removed, of the device of FIG. 5 which is useful in understanding the actuator mechanism.
Figure 7:
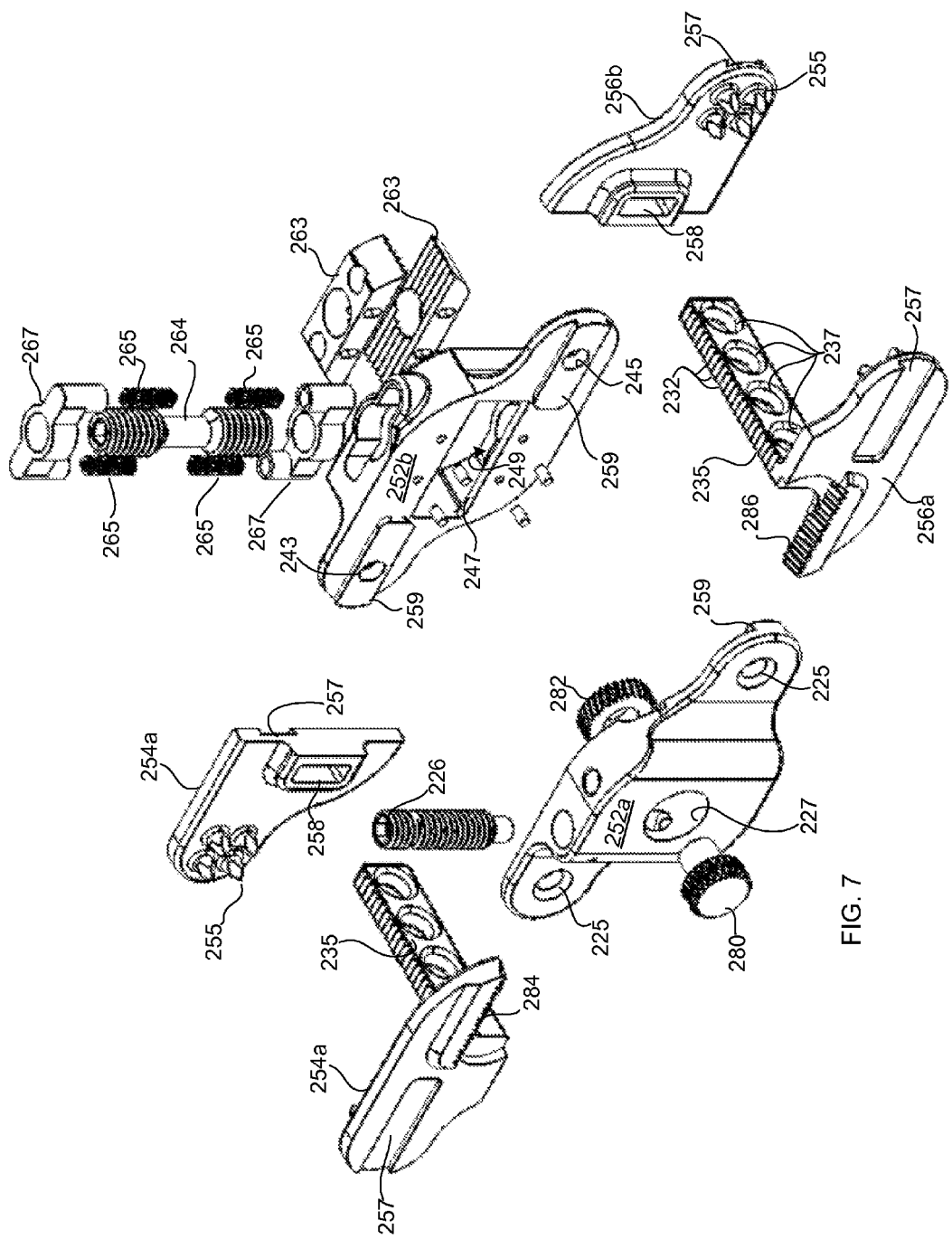
FIG. 7 is an exploded view of one particular embodiment of the device of FIG. 5.
Figures 8A, 8B:
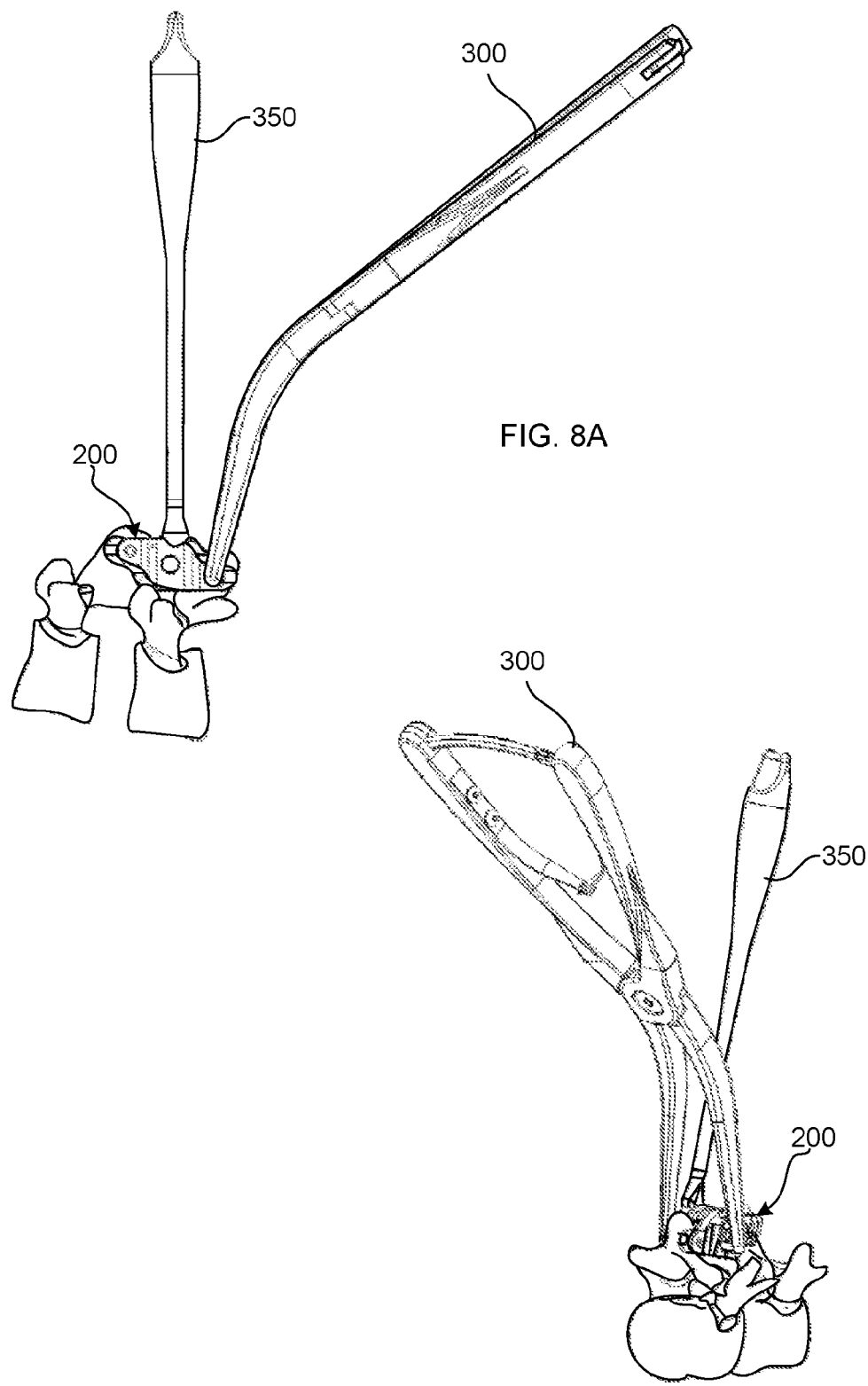
FIGS. 8A and 8B are a side plan view and a rear perspective view, respectively, of a system for installing an interspinous device such as the interspinous device of FIG. 5.

Referring now to FIGS. 5-7, there will now be described another embodiment of an interspinous fixation device 200 of the present invention, shown in an expanded configuration. As with the interspinous fixation device of FIGS. 3-4B, the interspinous fixation device 200 of the present invention may be inserted through a small incision at the location of the vertebrae to be fused, is adaptable to a wide variation between patient anatomies (for example, the distance between adjacent spinous processes), and fosters optimal bone growth to facilitate fusion between adjacent vertebrae. Further, operation time and recovery time are less than those of currently known methods. As discussed above, the interspinous fixation device 200 is preferably composed of biocompatible materials such as titanium, stainless steel, and/or polyetheretherketone (PEEK), although other materials may also be used.

As shown in FIGS. 5-7, the interspinous fixation device 200 includes a first plate 220 connected with a second plate 240, by a plurality of expansion or guide rods 235. Each of the first plate 220 and second plate 240 are made up of a plurality sub-plates or portions, including an outer fixed portion 252 and two movable inner expansion portions 254 and 256. Each of the inner expansion portions 254, 256 are connected with, and slidable relative to, its supporting outer plate 252 and include a plurality of sharp, pointed fixing studs 255 that may engage (that is, penetrate) bones, such as a spinous process. In the present particular embodiment shown, the inner expansion portions 254, 256 are slidably engaged with the outer fixed portions 252 using a slot 257 of the inner plate 254, 256 engaged with a slide block 259 of the outer fixed portion 252, or vice versa. Note that this is not meant to be limiting, as other mechanisms for slidably attaching the inner expansion portions 254, 256 to the outer fixed portions can be used without departing from the scope and spirit of the present invention.

In the present particular embodiment of the invention, the sliding of the inner expansion portions 254a, 256a of the first plate 220, controls the sliding of the inner expansion portions 254b, 256b, and thus, the expansion of the second plate 240. More particularly, each of the inner expansion portions 254a, 256a of the first plate 220 includes a first end of a guide rod 235 affixed thereto at a shoulder 234. The guide rods 235 may be integrally formed with the inner expansion portions 254, 256, or may be joined to them after formation, such as by a joint or weld, as desired. In the present particular embodiment, the first end of each guide rod 235 is permanently affixed to an inner surface (i.e., the surface opposite the one connected to the outer fixed portion) of the respective inner plate 254a, 256a. As in the previous embodiments, the guide rods 235 of the present embodiment may have a rectangular or square cross-sectional shape. However, this is not meant to be limiting, as other shapes, including but not limited to oval and/or circular, may be used, if desired. Additionally, in one particularly preferred embodiment, each of the guide rods 235 are provided with windows 237 therethrough, in which biologic material can be placed to promote bony ingrowth of the device 200. As discussed in connection with the above-described embodiments, if desired, each guide rod 235 may also have at least one ridged or serrated edge 232. In the present preferred embodiment, both of the top and bottom edges of the guide rods 235 include serrations 232.

The free end of each of the guide rods 235 passes through a fitted aperture or opening 258 through a respective one of the inner expansion portions 254b, 256b of the second plate 240, as well as through a large central opening 257 of the outer fixed portion 252b of the second plate 240. The shape and size of the fitted openings 258 should closely match the cross-sectional shape of the guide rods 235 (with allowance being made for any serrations or grooves 232 optionally included thereon), so that the plates 254b, 256 abut and/or substantially surround the guide rods 235. In this way, movement of the inner expansion portions 254b, 256b of the second plate 240 drives the movement of the inner expansion portions 254a, 256a of the first plate. In other words, in operation, the inner expansion portions 254a and 256a of the first plate pushes or pulls the respectively linked inner plate 254b, 256b together or apart, through the interaction between the guide rods 235 and the walls (in particular, the vertical walls) of the opening 258. Further, each guide rod aperture 258 may have a height that is only slightly greater than the height of each guide rod 235 to prevent movement in non-lateral directions.

Additionally, the interspinous fixation device 200 of the present particular embodiment includes a gearing mechanism for moving the inner expansion portions 254, 256 of the device from a retracted configuration into an expanded configuration, as described in more detail above. Although the device 200 is generally referred to herein as being in either the retracted or expanded configuration, it will be understood that the device 200 may be in any intermediate configuration therebetween, depending on the anatomy of the patient. For example, the device 200 may be partially expanded for fixation of vertebrae with an average space between adjacent spinous processes, and in a retracted configuration for fixation of vertebrae with a smaller-than-average space between adjacent spinous processes.

The gearing mechanism for expanding or contracting the present particular embodiment of the device 200 includes a worm gear 226, a first gear 280, a second gear 282 and the worm teeth 284, 286 of the inner expansion portions 254a, 256a, respectively. More particularly, the worm gear 226 is located through a hole in the outer fixed portion 252a of the first plate 220 and the thread of the worm gear 226 is meshed with the teeth of the first gear 280, which in the present particular embodiment, is a spur gear. One end of the worm gear 226 includes a hexagonal or other type of socket accessible through a hole in the top of the outer fixed portion 220, which can be used to rotate the worm gear 226 and to, correspondingly, drive the first gear 280 disposed in a chamber or housing 227 of the outer fixed portion 252a. The first gear 280 is linked by a shaft to the second gear 282, such that rotation of the first gear 280 also causes the concentrically mounted second gear 282 to rotate. The second gear 282 is aligned and enmeshed with the worm teeth 284, 286 of the inner expansion portions 254a and 256a, respectively, of the first plate 220, as shown more particularly, in FIGS. 6E and 6F. In one particularly preferred embodiment of the invention, three teeth of the first gear 280 are engaged with the worm gear 226 and three teeth of the second gear 282 are engaged with each set of worm teeth 284, 286 at all times. Additionally, in one particular embodiment of the invention, the second gear 282 is a helical gear having an angle complementary to the angles of the worm teeth 284, 286.

As can be seen, rotation of the second gear 282 in a first direction moves the inner expansion portions 254a, 256a apart, while rotation in a second direction, counter to the first direction, moves the inner expansion portions 254a, 256a closer together. Thus, in operation, rotation of the worm gear 226 using a wrench or driver in the socket thereof will rotate the first and second gears 280, 282, and move the inner expansion portions 254a, 256b apart or together relative to one another, depending on the direction in which the wrench or driver is turned. Additionally, because of the linkage between the inner expansion portions 254a, 256a of the first plate 220 and the inner expansion portions 254b, 256b of the second plate 240, rotation of the worm gear 226 will also result in a corresponding relative movement of the inner expansion portions 254b, 256b of the second plate 240. Although one particular gearing mechanism for the device 200 is disclosed herein, the present invention should not be limited only to the exact gear combination shown, as it should be understood that various other gear combinations can be used to produce the same results without departing from the spirit of the present invention.

Referring back to FIGS. 5-7, the present embodiment of the interspinous fixation device 200 further includes a locking ratchet mechanism or clamp for locking the two plates 220, 240 relative to one another after compression of the device 200, in use. More particularly, as discussed above, the free ends of the two guide rods 235, after passing through the openings 258, pass through a central opening 247 of the outer fixed portion 252b of the second plate 240. The outer fixed portion 252b includes a cavity 249 that forms a housing for, or frames, the opposing jaws of the clamp or vice members 263 of the ratchet mechanism, which are spring loaded by springs 265 against the serrated edges of the guide rails 235 (See, for example, FIG. 6D). Interaction between the serrations 232 on the guide rails 235 and correspondingly oriented ridges on the gripping surfaces of the vice members 263 provide a tactile ratchet mechanism that maintains the spacing between the first and second plates 220, 240, after compression. A double threaded locking screw 264 set into the frame of the outer fixed portion 252b and is used to tighten the vice members 263 against the guide rods 235, such that ridges or serrations of the ratchet locking mechanism 263 engage the serrations 232 on the guide rods 235. Once the proper device width is established, the screw 264 is tightened locking the ratchet mechanism 263 against the guide rods 235. As a non-limiting example, the locking screw 264 may include a hexagonal socket in at one or both ends (as shown in FIGS. 6A and 6B), although other mechanisms may be used.

Referring now to FIGS. 5-10, a device 200 of the present invention can be implanted into a patient according to the following method. First, the spinous processes of two or more vertebrae of interest may be accessed using any currently known method (for example, ALIF or TLIF methods). However, a procedure that is less invasive than many currently known methods may be used in conjunction with this device, since only a small incision is required to position the device, and use of the device may provide equal or greater biomechanical stability to the treated spinal segment than use of more invasive procedures with additional instrumentation. Once the spinous processes of interest are accessed, the first plate 220 and second plate 240 may be manually separated a distance such that the spinous processes of interest may be received between the first plate 220 and second plate 240. This width is particular to the anatomy of the patient.

The device 200 may be positioned such that the fixing studs 255 engage at least a portion of each of the adjacent spinous processes. If the device 200 needs to be adjusted to a more retracted or a more expanded configuration, the worm gear 226 may be rotated using a tool configured to engage the head of the worm gear 226. As can be seen, rotation of the worm gear 226 will, ultimately, move the inner and outer fixed portions 254, 256 closer together or further apart, depending on the direction of rotation of the worm gear 226. More particularly, the worm gear 226 will rotate the first gear and second gears 180, 182, the second gear 182 will drive the inner and outer fixed portions 254a, 256a of the first plate 220, via the worm teeth 284, 286, and, simultaneously, the guide arms 235 will move the inner and outer fixed portions 254b, 256b of the second plate a corresponding amount. Rotation of the worm gear 226 is performed to adjust the amount that the inner expansion portions are separated relative to one another in order to fit the particular anatomy of the patient.

Once the plates 120, 140 are separated to a sufficient distance, the device may be positioned on the spinous processes such that the fixing studs 255 of the inner expansion portions 254, 256 of the first and second plates 220, 240 are in contact with at least a portion of each spinous process. For example, the device may be positioned using an implant delivery instrument 350 having a finger 352 that matingly engages a hole 221 in the first plate 220 of the interspinous fixation device 200. More particularly, the implant delivery instrument 350, when mated to the device 200, can be used to easily adjust the position of the device 200 relative to the spinous processes inside the incision and can also be used to hold the device 200 in place during compression. Further, the guide rods 235 may be disposed between the adjacent processes, so that they do not interfere with the patient's anatomy. The expansion of the device 200 is manually adjusted to place the fixing studs 255 in contact with the adjacent processes, as will be determined by individual patient anatomy. Once the fixing studs 255 of the device 200 sufficiently line up with each of the adjacent processes, one or more compression clamps 300 may be used to provide a compression force on the first plate 220 and second plate 240 of the device, thereby squeezing the interspinous fixation device 200 tightly about the adjacent processes such that the fixing studs 255 penetrate the bone. More particularly, one or more standard, ratcheting compressor clamp(s) (300 of FIGS. 8A, 8B) may be used to squeeze together the first and second plates 220, 240, thus driving the studs 255 into the bone. Alternately, one or more specialized tools, such as the clamp 320 of FIG. 9, can be used in place of the standard clamps 300. Clamp 320 includes opposing jaws 322, 324, each of which has a pin or nipple 326 at the distal end. The pin 320 can be engaged with holes 225, 245 of the outer fixed portions 252, in order to more securely hold and compress the plates 220, 240 together.

After compression, the locking screw 264 may be rotated to engage the vice members 263 with serrations 232 of the guide rods 235, thereby locking the interspinous fixation device 200 in place. Once the device 200 is in place, spinal distraction may be accomplished by rotating the worm gear 226 to increase the distance between (i.e. distract) the adjacent vertebrae. Graft material (allograft or autograft) may be inserted into the space created between the first plate and second plates 220, 240 of the device 200 when the first and second plates 220, 240 are spread a distance apart by the spinous processes of adjacent vertebrae. Graft material may also be inserted in spaces around the device 200 and/or in the windows 237 of the guide bars 235. The combination of the device placement and the graft material disposed within the device 200 eventually will lead to the fusion of the vertebrae connected by the device 200.

In most procedures, the interspinous fixation device of the present invention may be inserted through a small incision at the location of the vertebrae to be fused. Unlike many previously known devices (such as dynamic stabilization systems that allow for controlled movement of the affected segment of the spine), the interspinous fixation device of the present invention is intended for fixation only, and not for motion prevention. Further, the interspinous fixation device shown and described herein is more adaptable to a wide variation between patient anatomies (for example, the distance between adjacent spinous processes), and fosters optimal bone growth to facilitate fusion between adjacent vertebrae. Further, operation time and recovery time are less than those of currently known methods.

The present interspinous fixation device may advantageously be used for common procedures instead of previously known devices. For example, the present interspinous fixation device may be used for posterior interlaminar fusion, posterolateral fusion, anterior lumbar interbody fusion (ALIF), transforaminal lumbar interbody fusion (TLIF), TLIF with unilateral pedicle screws, hybrid constructs and/or revision procedures, and direct lateral procedures.

In known methods of posterior interlaminar fusion, direct decompression is first performed on the patient. That is, a small portion of the arch of a vertebral bone (laminectomy) is removed to alleviate pressure on a compressed nerve. Additionally, the intervertebral disc material may be removed and replaced with a bone graft. The vertebrae of interest may be reached through an incision in the patient's back, and the spinal muscles may be retracted (separated) to allow access to the vertebral disc and nerves. In a method involving the interspinous fixation device according to the present invention, the bone material from the decompression may be inserted within an aperture in the inventive interspinous fixation device, and the interspinous fixation device can then be clamped over the posterior spinous processes of, for example, two adjacent vertebrae, the device serving as posterior instrumentation. Fusion may result between the posterior medial segments (including facet joints), laminae, and within a central load-sharing adjustable aperture of the present, inventive interspinous fixation device. Thus, the biomechanical strength of the present inventive device, on a per-segment basis, is superior to previously known devices. Further, the present inventive device will also stabilize the foraminal height.

Posterolateral fusion, which is more invasive than posterior interlaminal fusion, typically involves the transverse processes of the vertebrae. Conservative direct decompression and sparing of the posterior processes may first be performed, and graft material may be inserted between the transverse processes. The present device may then be affixed to the posterior processes as shown and described in FIGS. 1 and 2. In this procedure, the present device may be a posterior, non-pedicle, supplemental fixation device that offers an alternative to pedicle screw instrumentation. Thus, many of the risks involved with pedicle screws (such as cerebrospinal fluid leakage, nerve pathology, and infection) may be eliminated.

In previously known methods of ALIF, the vertebrae of interest are accessed from the front (anterior) side of the body, usually though an incision in the lower abdomen or the side. Other methods involve the use of an anterior fusion device in conjunction with support with posterior instrumentation. Although pedicle screw fixation is currently the gold standard for creating a rigid stabilizing construct for the lumbar spine, it is associated with risks including cerebrospinal fluid leakage, nerve pathology, and infection. However, use of an interspinous fixation device of the present invention, in conjunction with ALIF, provides superior stability without the risks of previously known methods.

In previously known methods of TLIF, the vertebrae of interest are approached from a side angle, which reduces the amount of surgical muscle dissection and minimizes the nerve manipulation required to access the vertebrae, discs, and nerves. Use of the an interspinous fixation device of the present invention may provide biomechanical stability that is comparable to the use of unilateral pedicle screws, thereby reducing the likelihood and/or severity of side effects associated with pedicle screws. In an alternative and somewhat more invasive TLIF method, circumferential arthrodesis may be possible with a single posterior approach through the foramen. For this procedure, bilateral pedicle screws are typically used. However, use of an interspinous fixation device according to the present invention with this TLIF procedure may provide equivalent or superior biomechanical stability with the use of only unilateral pedicle screws, thereby reducing the likelihood and/or severity of side effects associated with pedicle screws.

In previously known direct lateral methods, a lateral approach in support of lumbar fusion may circumvent vascular and neural risk associated with anterior and posterior approaches while also offering the patient a minimally invasive alternative to anterior column access. Bilateral pedicle screws are typically used to stabilize the vertebrae once the graft material is implanted between the vertebrae of interest. Use of an interspinous fixation device according to the present invention provides equivalent or superior biomechanical stability to an ALIF procedure utilizing bilateral pedicle screws. Therefore, use of the present device may eliminate the need for bilateral pedicle screws, thereby reducing the likelihood and/or severity of side effects associated with pedicle screws.

In hybrid constructs and/or revision procedures, multiple fixation devices may be used to achieve segmental stability. The presently described, inventive interspinous fixation device may be used in conjunction with facet screws, anterior plates, lateral plates, and/or pedicle screws if necessary. Further, when complex revision anatomy is encountered, posterior fixation using the present device may easily facilitate the fixation needs of a patient at his or her adjacent levels and could therefore eliminate the need to review previously placed hardware. Thus, the complexity, trauma, and/or extent of a given revision procedure may be greatly reduced.

Additionally, an interspinous fixation device made in accordance with the present invention (as described herein) has the added advantage that it can be adjusted, post-operatively, in a minimally invasive manner. More particularly, after implantation and recovery, the interspinous fixation device of the present invention can be accessed by a surgeon in a minimally invasive manner to readjust the position of the device. This may be useful in cases of a post-operative fracture or failure of a particular spinous process to which the device was previously mounted. In such a case, the patient could have the attachment/positioning of the device adjusted at a clinic, ambulatory surgery center or other outpatient setting.

Referring back to FIGS. 1-8, in one particular embodiment of the invention, the device 10, 100, 200 of FIGS. 1-8 is configured so as to be adjusted at a later time after implantation through a percutaneous outpatient procedure. More particularly, a patient needing an adjustment of the device can be by positioned using a C-arm so that the interspinous fixation device 10, 100, 200 were accessible to a surgeon. During the procedure, the surgeon can use a tool, percutaneously, to engage the head of the worm gear 126, 226 to permit expansion and/or contraction of the device 10, 100, 200. If necessary and/or desired, the head of the ratchet mechanism screw 164, 264 could also be accessed in this way to lockdown or loosen that mechanism and/or to adjust the width of the device. In one particular embodiment of the invention, the hole providing access to the head of the worm gear 126, 226 can be provided with a targeting device or a funnel-like entry in order to guide a driver tool into the worm gear head. In another particular embodiment of the invention, head of the worm gear 126, 226 (and, optionally, the head of the ratchet screw 164, 264) is cannulated, so that a wire can be inserted into the cannulated portion of the head to clean out the head and to guide a cannulated driver into a docked position. Once the driver is engaged with the head of the worm gear 126, 226, the surgeon can re-adjust or fine-tune the device, even years after the original implantation of the device.

While a preferred embodiment of the present invention is shown and described herein, it will be understood that the invention may be embodied otherwise than as herein specifically illustrated or described, and that within the embodiments certain changes in the detail and construction, as well as the arrangement of the parts, may be made without departing from the principles of the present invention as defined by the appended claims.

We claim:

1. An expandable interspinous fixation device, the device comprising:
    a first expandable plate, including:
        a first outer fixed portion, a first inner expansion portion and a second inner expansion portion, said first inner expansion portion and said second inner expansion portion being connected to said first outer fixed portion and slidable relative to one another;
    a second expandable plate, including:
        a second outer fixed portion, a third inner expansion portion and a fourth inner expansion portion, said third inner expansion portion and said fourth inner expansion portion being connected to said second outer fixed portion and slidable relative to one another;
    a mechanical actuator linked to at least said first and second inner expansion portions to move said first inner expansion portion relative to said second inner expansion portion when operated;
    said mechanical actuator including a first gear engaged with teeth on said first and second inner expansion portions, wherein rotation of said first gear moves said first and second inner expansion portions relative to one another;
    said first gear and the teeth on said first and second inner expansion portions forming a worm drive mechanism;
    said mechanical actuator further including:
        a second gear disposed in a housing of said first outer fixed portion and linked to said first gear, wherein rotation of said second gear drives said first gear; and
        a third gear engaged with the second gear, wherein rotation of said third gear drives said first and second gears;
    wherein the third gear is a worm gear and the third and second gears form a worm drive, wherein rotation of said worm gear results in a linear sliding movement of at least said first and second inner portions.

2. The device according to claim 1, wherein said mechanical actuator is additionally linked to said third inner expansion portion and said fourth inner expansion portion to directly move said third inner expansion portion relative to said fourth inner expansion portion when operated.

3. The device according to claim 1, wherein actuation of said mechanical actuator simultaneously moves both of said first inner expansion portion and said second inner expansion portion relative to one another.

4. The device according to claim 3, further including a first linkage between said first inner expansion portion and said third inner expansion portion and a second linkage between said second inner expansion portion and said fourth inner expansion portion, wherein said third and fourth inner expansion portions are moved simultaneously with said first and second inner expansion portions by said first and second linkages.

5. The device according to claim 4, further including a locking mechanism including a locking bracket, wherein said first and second linkages are guide rails passing from said first and second inner expansion portions through said third and fourth inner expansion portions and said locking bracket.

6. The device according to claim 5, wherein said guide rails include serrations on at least one edge thereof and said locking bracket includes grooves complementary to said serrations, wherein said serrations and grooves are configured to form a ratchet permitting locking movement of said second expandable plate in the direction of the first expandable plate.

7. An expandable interspinous fixation device, the device comprising:
    a first expandable plate including a first plurality of sub-portions;
    a second expandable plate including a second plurality of sub-portions;
    a mechanical actuator including at least one worm drive mechanism for moving at least one sub-portion of said first plurality of sub-portions relative to at least one other sub-portion of said first plurality of sub-portions;
    the first plurality of sub-portions of the first expandable plate, including:
        a first inner expansion portion and a second inner expansion portion, said first inner expansion portion and said second inner expansion portion being movable relative to one another;
    the second plurality of sub-portions of the second expandable plate, including:
        a third inner expansion portion and a fourth inner expansion portion, said third inner expansion portion and said fourth inner expansion portion being movable relative to one another; and
    each of the first inner expansion portion and the second inner expansion portion including gear teeth engaged with a first gear to move the first and second inner expansion portions relative to one another upon rotation of said first gear;
    wherein said first inner expansion portion and said third inner expansion portion are linked together by a first guide rail and said second inner expansion portion and said fourth inner expansion portion are linked by a second guide rail, such that movement of said first and second inner expansion portions causes a resultant movement of said third and fourth inner expansion portions due to movement of said first and second guide rails; and
    wherein said worm drive mechanism includes a first worm gear driven from outside the device, said first worm gear engaged with a second gear, said second gear engaged to said first gear.

8. The device according to claim 7, further including a locking mechanism including a locking bracket, wherein said guide rails include serrations on at least one edge thereof and said locking bracket includes grooves complementary to said serrations, wherein said serrations and grooves are configured to form a ratchet permitting locking movement of said second expandable plate in the direction of the first expandable plate.

9. A method for fusing adjacent vertebrae, the method comprising:
    providing a device according to claim 1;
    enclosing the spinous process of each of two adjacent vertebra between the first expandable plate and the second expandable plate of the interspinous fixation device; and
    adjusting the position of the first inner expansion portion relative to the second inner expansion portion and the third inner expansion portion relative to the fourth inner expansion portion.

10. A method for adjusting an interspinous fixation device implanted in a patient, wherein the interspinous device is the device according to claim 1, the method comprising:
    percutaneously accessing a driver portion of the mechanical actuator with a driver tool; and adjusting the position of the first inner expansion portion relative to the second inner expansion portion and the third inner expansion portion relative to the fourth inner expansion portion of the implanted interspinous fixation device using the driver tool.

* * * * *